(12) United States Patent
Miyaoka et al.

(10) Patent No.: US 8,002,702 B2
(45) Date of Patent: Aug. 23, 2011

(54) ULTRASONOGRAPH AND METHOD FOR CONTROLLING MOVEMENT OF DISPLAY BODY OF ULTRASONOGRAPH

(75) Inventors: Takehiro Miyaoka, Chiba (JP); Masaru Suemune, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1721 days.

(21) Appl. No.: 10/528,656

(22) PCT Filed: Sep. 26, 2003

(86) PCT No.: PCT/JP03/12326
§ 371 (c)(1),
(2), (4) Date: Oct. 6, 2005

(87) PCT Pub. No.: WO2004/028372
PCT Pub. Date: Apr. 8, 2004

(65) Prior Publication Data
US 2006/0100519 A1 May 11, 2006

(30) Foreign Application Priority Data

Sep. 27, 2002 (JP) .................. 2002-283706

(51) Int. Cl.
*A61B 8/00* (2006.01)
(52) U.S. Cl. ........................ 600/437; 382/130
(58) Field of Classification Search .......... 600/437–461; 382/130–132
See application file for complete search history.

(56) References Cited

U.S. PATENT DOCUMENTS

| 5,533,510 A * | 7/1996 | Koch et al. ............... 600/443 |
| 5,538,004 A * | 7/1996 | Bamber ................... 600/443 |
| 5,800,356 A * | 9/1998 | Criton et al. ............. 600/441 |
| 5,873,830 A * | 2/1999 | Hossack et al. .......... 600/447 |
| 6,193,660 B1 * | 2/2001 | Jackson et al. .......... 600/443 |
| 6,688,177 B2 * | 2/2004 | Wiesauer ................. 73/618 |
| 6,878,114 B2 * | 4/2005 | Murashita ............... 600/443 |
| 7,695,439 B2 * | 4/2010 | Jackson et al. .......... 600/450 |
| 2002/0087061 A1 | 7/2002 | Lifshitz |

FOREIGN PATENT DOCUMENTS

JP 63-105089 7/1988

* cited by examiner

*Primary Examiner* — Sanjay Cattungal
(74) *Attorney, Agent, or Firm* — Antonelli, Terry, Stout & Kraus, LLP.

(57) ABSTRACT

The operability of setting movement of a Doppler sample gate for setting a Doppler measurement portion on a sectoral or circular ultrasonogram is improved. An ultrasonograph is provided with calculation means (25) for determining the position where a Doppler sample gate is displayed after the gate is moved, with reference to the current position where the Doppler sample gate is displayed, according to the amount of movement of the Doppler sample gate position input through a tack ball (23). The calculation means decomposes the amount of movement in orthogonal two-axis direction input through a track ball (23) into a component in the direction of the ultrasonic beam line of an ultrasonogram and a component orthogonal to the former component, determines the ultrasonic beam line after the movement from the decomposed orthogonal components, determines the depth position of the ultrasonic beam line after the movement from the decomposed component in the ultrasonic beam line direction, and changes the display position of the Doppler sample gate to the determined display position after the movement. Thus, the movement of the Doppler sample gate corresponds to the operation of the track ball on the screen irrespective of the position in the sectoral or circular display area, thereby mitigating the feeling of strangeness and improving the operability.

20 Claims, 8 Drawing Sheets

TRACK BALL

ULTRASONOGRAPH AND METHOD FOR CONTROLLING MOVEMENT OF DISPLAY BODY OF ULTRASONOGRAPH

TECHNICAL FIELD

This invention relates to an ultrasonograph and a method for controlling movement of a display body of the ultrasonograph. More particularly, this invention relates to improvement in controlling movement of a display body showing a measurement portion such as a Doppler sample gate, an interest area, etc., on an ultrasonogram.

BACKGROUND ART

When a blood flow velocity, etc., are measured, as described in Japanese Patent No. 3403917, for example, an ultrasonograph displays a color flow mapping image showing the state of a blood flow such as the movement of a blood flow, the direction of a blood flow, etc., superimposed on an ultrasonic image (B image) of a diagnostic portion. This color flow mapping image is generated in a Doppler color box (interest area) set on the B image. Then, a Doppler sample gate (display mark) superimposed on a blood vessel in the color flow mapping image in the Doppler color box is displayed and a blood flow velocity, etc., are measured based on a reflection echo signal of an area sandwiched in a Doppler sample gate. These Doppler sample gate and Doppler color box are generally set such that the display position on a screen is moved by a pointing device such as a track ball, etc.

Now, ultrasonic images and color flow mapping images obtained from the ultrasonograph are generally displayed in the shape of a sector (for example, the central angle of a sectoral image is 30 to 120°). In a tack ball, for example, it is made that the amount of movement in the vertical direction of a display image corresponds to the depth position of an ultrasonic beam line and the amount of movement in the horizontal direction corresponds to the scanning direction of the ultrasonic beam line.

However, along the development of ultrasonic diagnostic technology, there are cases where images of a wide visual field or of a sectoral portion of a wide central angle (for example 180° or more) are obtained. For example, there is a case where an ultrasonic probe in which ultrasonic transducers are provided around a cylinder and which can perform an omni-directional scanning (360°) is inserted into a coelom such as an esophagus, an ultrasonic beam is radiated from the ultrasonic probe in the center, and a circular ultrasonic image seen from the inside of the coelom is obtained.

While such a sectoral or circular image of a wide visual field is seen, when the Doppler sample gate and the interest area are moved by a conventional operating method, since the operating direction of the track ball is greatly different from the target direction of a Doppler sample gate on the screen, there is a problem in that the feeling of strangeness is caused in the operation of the track ball and the operability is lowered.

Such a problem in the operability for setting the position of a display mark is not limited to the Doppler sampling gate, and there is the same problem in the operation of movement of an interest area such as a color box in the color flow mapping, etc.

It is an object of the present invention to improve the operability in movement of a display body designating a measurement portion, etc.

DISCLOSURE OF INVENTION

In order to attain the above object, an ultrasonograph of the present invention comprises an ultrasonogram generating portion for generating an ultrasonogram based on a reflection echo signal obtained by radially scanning a specimen irradiated with an ultrasonic beam and a display area; a monitor screen for displaying the generated ultrasonogram; a display-body image generating portion for generating an image of a display body superimposed on the ultrasonogram; means for storing a first display position of the display body displayed on the monitor screen; an input portion for inputting the amount of movement of the display body from the first display position to a second display position; calculation means for determining the second display position of the display body based on the amount of movement input from the input portion and the display area; and means for moving the display body from the first display position to the second display position determined by the calculation means.

In this way, according to the present invention, since the display position of a display body is moved such that a second display position of the display body is determined based on the amount of movement from a first display position of the display body to the second display position input from an input portion, when the vertical and horizontal positions on a monitor screen are set to be the same as the vertical and horizontal directions in the input portion, the display body can be moved substantially in the same direction on the screen as the operation in the input portion regardless of the position on the display area. That is, when the input portion is operated in the same direction as the direction of movement on the image, since the direction of movement does not change in spite of the position of the display body, the sense of strangeness of the operator is reduced and the operability can be improved.

In this case, since it is made that the calculation means contains a storage portion for storing the first (current) display position of the display body through the position of an ultrasonic beam line and a depth on the ultrasonic beam line, and then, it is desirable to determine the second display position (after movement of the display position) by making use of the position of the ultrasonic beam line and the depth on the beam line. For example, it is desirable that the calculation means decompose the amount of movement input from the input portion into a component in the direction of the ultrasonic beam line of the ultrasonogram and a component orthogonal to the former component, the ultrasonic beam line of the second display portion be determined based on the component orthogonal to the former component, and the depth position on the ultrasonic beam line of the second display position be determined based on the component in the direction of the ultrasonic beam line.

Furthermore, the calculation means determines a second display position of the display body based on a coordinate transformation rule set in advance, and the coordinate transformation rule is separately set for a case where the central angle of a sectoral or circular portion of the ultrasonogram is a set value or less and for a case where the central angle of the sectoral or circular portion of the ultrasonogram is above the set value. In this case, the coordinate transformation rule contains a first coordinate transformation rule to be applied to a case where the central angle of a sectoral portion of the ultrasonogram is a set value (for example, 120°) or less and a second coordinate transformation rule to be applied to a case where the central angle of the sectoral or circular portion of the ultrasonogram is above the set value (for example, 120°). In the first coordinate transformation rule, the direction of one axis of the amount of movement input from the input portion corresponds to a depth in the direction of an ultrasonic beam line and the direction of the other axis corresponds to the direction orthogonal to the direction of the ultrasonic beam line. In this case, in the second coordinate transformation rule, the amount of movement input from the input portion is decomposed into a component in the direction of an ultrasonic beam line and a component orthogonal to the ultrasonic beam line, an ultrasonic beam line at a second display position of the display body is determined based on the component orthogonal to the ultrasonic beam line, and a depth position of the ultrasonic beam line at the second display portion is determined based on the component in the direction of the ultrasonic beam line.

Here, the display body of the present invention can be applied to a mark showing the position of a Doppler sample gate, a Doppler color box, and a M-mode sample gate. A color flow mapping image showing the state of a blood flow generated by the ultrasonogram generating portion can be displayed in an area marked off by a Doppler color box. Furthermore, the display body of the present invention can be also applied to a boundary line which demarcates the area of a Doppler color box and a B-mode image pick-up area, or dots or a frame body designating a boundary. That is, in the case of a frame body, the area of a Doppler color box and a B-mode image pickup area can be changed, expanded, or reduced by moving one of boundary lines or an apex constituting a frame.

Furthermore, for example, a track ball, a mouse, a pressure-sensitive pad, an electrostatic pad, a joystick, a direction key in the keyboard, etc., can be given as an input portion, but the input portion is not limited to those and any one in which the amount of movement in orthogonal two-axis direction can be input may be used.

BEST MODE FOR CARRYING OUT THE INVENTION

Figure 1:
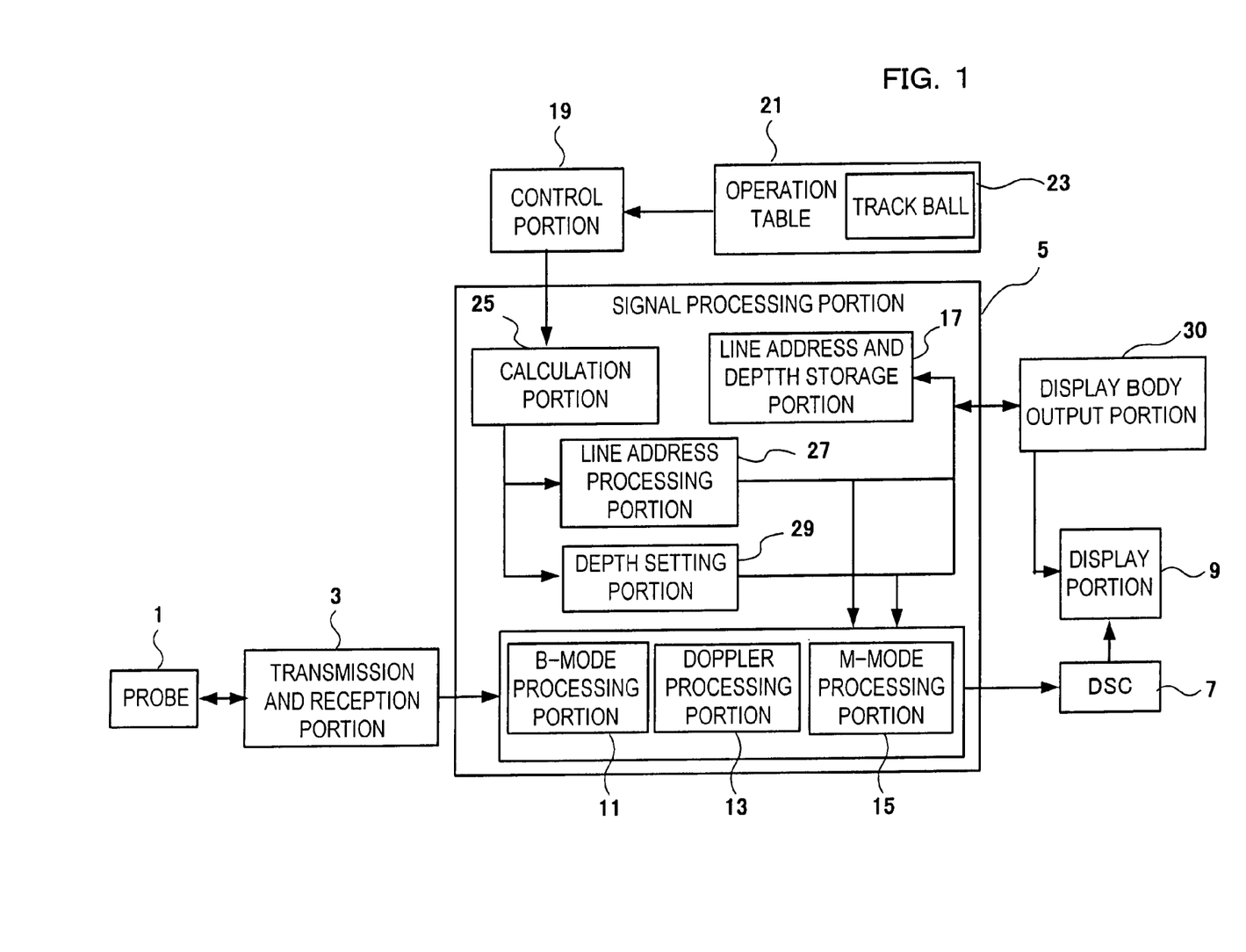
FIG. 1 is a block diagram showing the construction of an ultrasonograph of an embodiment of the present invention.

Hereinafter, an ultrasonograph of an embodiment of the present invention is described. FIG. 1 is a block diagram showing the construction of an ultrasonograph of the present embodiment. As shown in FIG. 1, the ultrasonograph contains a probe 1 having a plurality of ultrasonic transducers, a transmission and reception portion 3 in which transmission and reception of an ultrasonic signal are performed to and from a specimen (not illustrated) through the probe 1, a signal processing portion 5 in which a receiving signal (reflection echo signal) received by the transmission and reception portion 3 is processed and an ultrasonogram to be displayed in a fixed display area is generated, a digital scan converter (DSC) 7 in which a signal output from the signal processing portion 5 is scanned and converted to generate an ultrasonogram, and a display portion 9 having a monitor display displaying the ultrasonogram output from the DSC 7.

The signal processing portion 5 contains a B-mode processing portion 11, a Doppler processing portion 13, and a M-mode processing portion 15 to each of which the receiving signal output from the transmission and reception portion 3 is input. Furthermore, the signal processing portion 5 contains a line address and depth storage portion 17. In the line address and depth storage portion 17, the position or area of a display body which is superimposed on the ultrasonogram and displayed is stored in connection with a line address as the information of the direction of transmission and reception of an ultrasonic beam and a depth on the line address. Here, the display body includes, for example, a Doppler sample gate and a Doppler color box in Doppler-mode operation, the position of a sample gate in M-mode operation, and the area of a Doppler color box, a boundary line or a boundary point for fixing the scanning target area in B-mode operation, and others. Furthermore, the ultrasonograph contains a control portion 19 having a CPU therein and an operation table 21 connected to the control portion 19. The operation table 21 contains a track ball 23 as an input means for moving the display position of the display body. The track ball 23 obtains the movement of a ball rotated by an operator as an input signal or amount of movement in orthogonal two-axis direction.

Then, the signal processing portion 5 contains a calculation portion 25 in which the display position of the display body after movement is calculated based on a signal of the amount of movement input from the track ball 23 through the operation table 21 and the control portion 19. In the signal processing portion 5, a line address processing portion 27 in which the line address of the display body after movement is set in accordance with the display position of the display body after movement output from the calculation portion 25 and a depth setting portion 29 in which the depth of the display body after movement is set are provided. Furthermore, a display body output portion 30 in which, for example, an image of the display body of the Doppler sample gate, etc., is generated in accordance with the line address and the depth output from the line address processing portion 27 and the depth setting portion 29 and superimposed and displayed on the ultrasonogram output from the DSC 7.

Next, the operation of the above-described ultrasonograph is described. The transmission and reception portion 3 generates an ultrasonic transmission signal and supplies the signal to a plurality of ultrasonic transducers (not illustrated). Moreover, in the present embodiment, the probe 1 is a probe in which a plurality of strip-shaped ultrasonic transducers are circularly arranged on the side surface of a cylindrical main body and which can electronically scan 360° around the inside of a coelom such as a esophagus. An ultrasonic transmission signal is composed of signals of a plurality of channels corresponding to a number of ultrasonic transducers of a chosen bore for transmission. The ultrasonic transducers receiving the transmission signal vibrate to generate ultrasonic waves, respectively, and an ultrasonic beam proceeding in the specimen in the direction where a wave front of the ultrasonic waves are in agreement is generated. The ultrasonic beam is propagated in the specimen, a part of the ultrasonic beam is reflected at a location where the acoustic impedance on the surface of an internal organ, etc., changes, and a part of the ultrasonic echo as the reflected wave returns to the probe 1 once again and is received as a reflection echo signal by the transmission and reception portion 3. Furthermore, the transmission and reception portion 3 transmits and receives an ultrasonic wave in order while the angle of the direction of transmission of an ultrasonic wave is gradually changed (for example, one degree at a time), and the specimen is scanned 360 degrees from the inside of a coelom. That is, in the case of the present embodiment, the specimen is scanned by 360 ultrasonic beams in one round. Moreover, for convenience of signal processing, each beam position corresponding to the scanning position of an ultrasonic beam being transmitted and received is given an identification number or identification code called a line address.

In the B-mode processing portion 11 of the signal processing portion 5, an intensity-modulated B-mode image data is generated based on the reflection echo signal at the position of a picture element set in accordance with the line address and depth of a reflection echo signal. Moreover, the depth can be obtained based on the going and returning propagation time of an ultrasonic signal, that is, a time interval between transmission and reception. Then, the B-mode image data output by the B-mode processing portion 11 is input to the DSC 7, and scanning conversion is performed here and the B-mode image data is displayed as a B-mode image on the monitor display of the display portion 9.

The B-mode image to be displayed in the display portion 9 is a circular gap image sandwiched between a non-displayable area corresponding to the inner portion of the surface of the probe 1 and an outer non-displayable area determined in accordance with the ultrasonic pulse repetition frequency (PRF) to be transmitted from the probe 1. In the case of measuring blood flow information such as a blood flow velocity, etc., a well known color flow mapping image (see Japanese Patent No. 3403917, for example) showing the state of a blood flow and the direction of a blood flow is displayed. A Doppler sample gate superimposed on the color flow mapping image is displayed. Then, a measurement is performed such that the Doppler sample gate is moved and a measurement portion (position or area) is set. The measured Doppler mode measurement information is displayed as a Doppler image of an appropriate shape on the monitor display. The ultrasonograph of the present embodiment is characterized by the setting method of a position or area of the Doppler sample gate.

Figure 2:
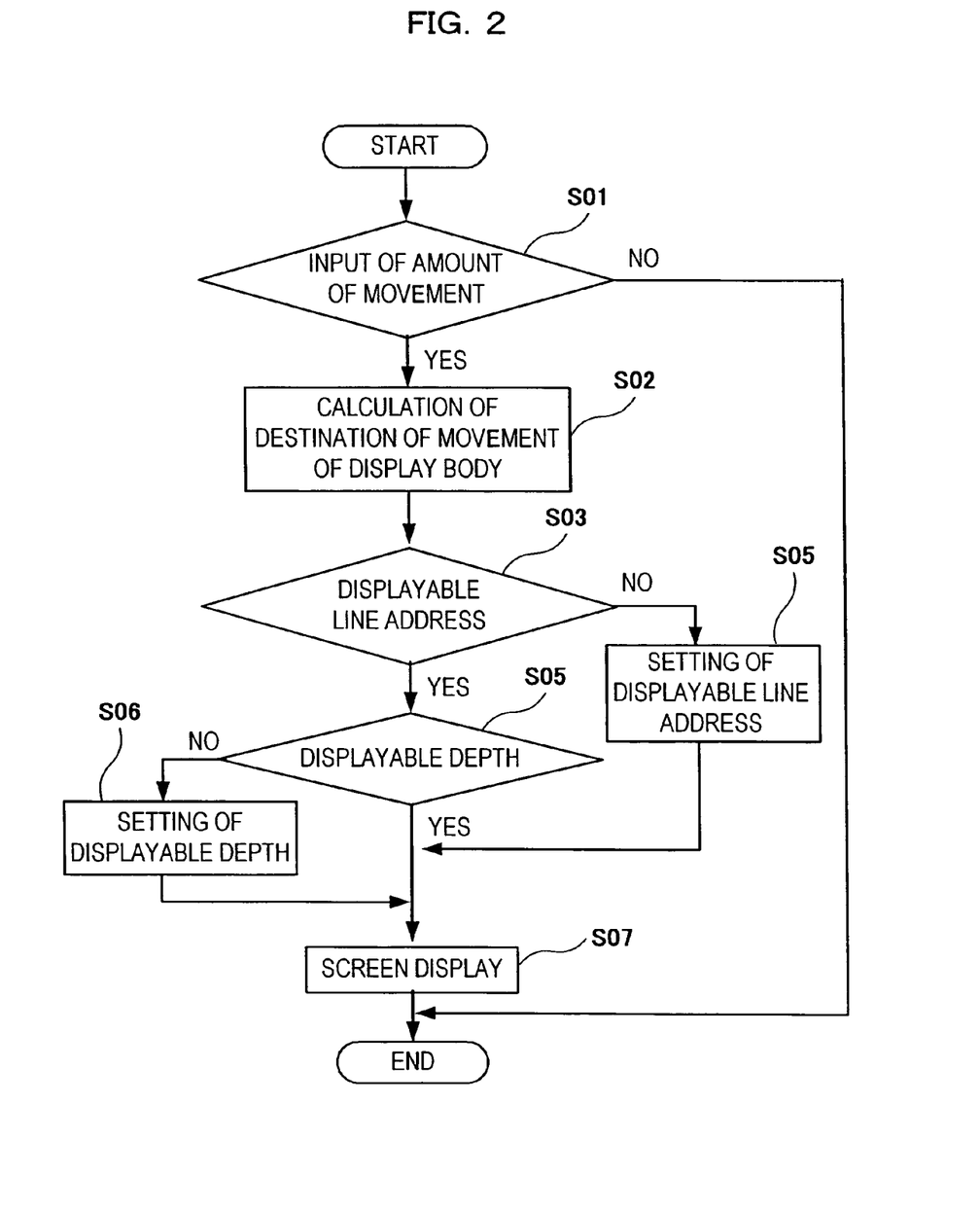
FIG. 2 is a flow chart showing a method for moving a Doppler sample gate by using the ultrasonograph in FIG. 1.
Figure 3:
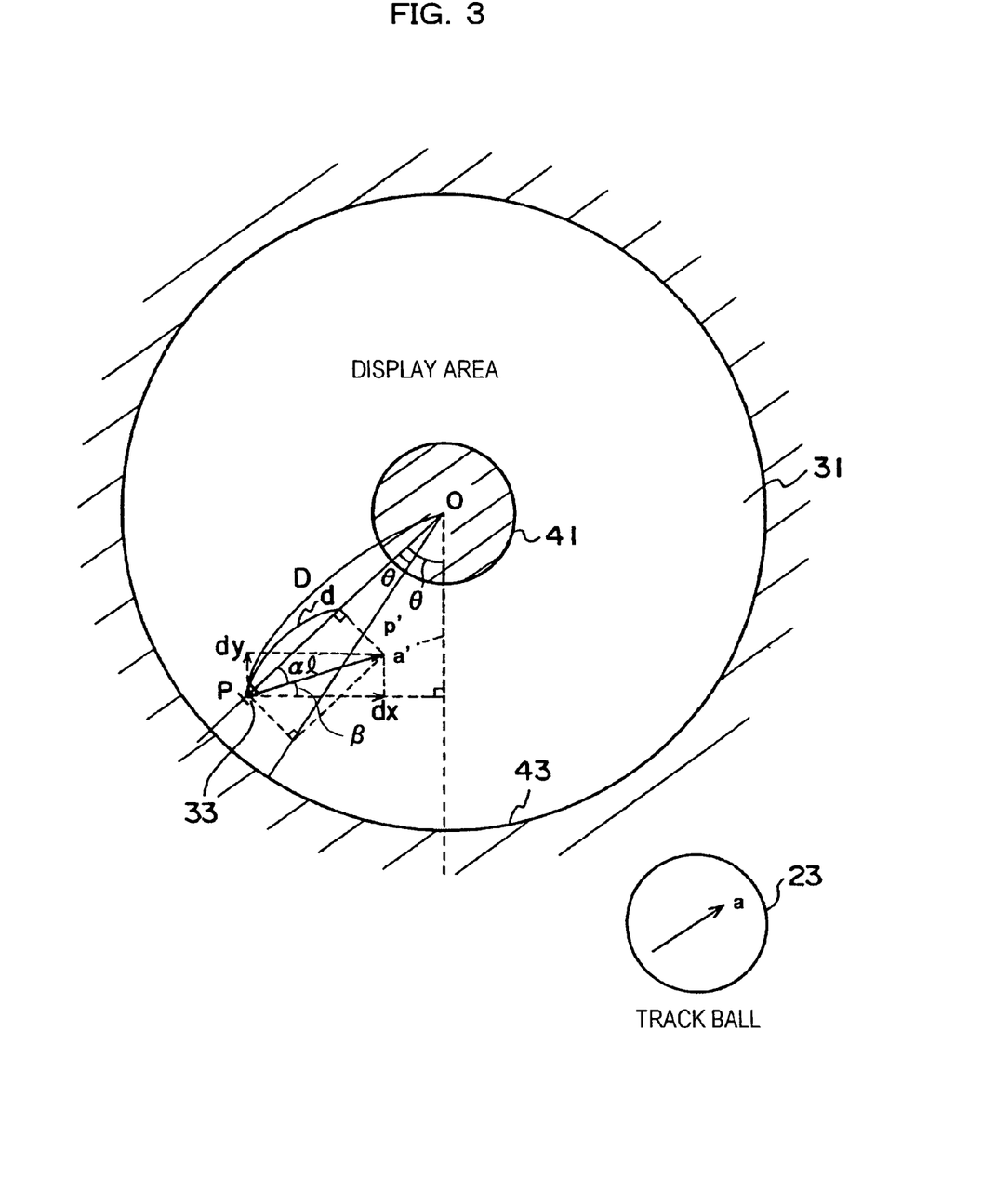
FIG. 3 shows one example of the operation and the screen display of a track ball in the ultrasonograph in FIG. 1 and a method for determining a line address and a depth after input.

FIG. 2 is a flow chart showing the steps of movement of a Doppler sample gate. As shown in FIG. 2, first of all, in step S01, the control portion 19 determines whether or not the amount of movement is input from the track ball 23. When there is an input, the process goes to step S02 where the display position of the display body after movement is calculated. On the other hand, when there is no input, the processing is finished. In step S02, the calculation portion 25 takes in the line address and depth regarding the position of a Doppler sample gate before movement held by the line address and depth storage portion 17 and the line address and depth of the destination of movement of the Doppler sample gate is calculated. In FIG. 3, one example of the operation of a track ball and a screen display and a method for obtaining the line address and depth of a Doppler sample gate after movement are shown. As shown in the drawing, the Doppler sample gate is composed of a pair of line bodies opposite to each other. The image of the Doppler sample gate is generated by the display body output portion 30 as a display body image generating portion, and the pair of line bodies are displayed so as to be orthogonal to the ultrasonic beam line. First, as shown in FIG. 3, it is assumed that the position of the Doppler sample gate 33 before movement was at point P on a circular ultrasonic image 31. At this time, it is also assumed that the operator makes an input equivalent to vector a by operating the track ball 23. The calculation portion 25 has a coordinate conversion rule for converting the input vector a to the amount of movement on the monitor display. In the coordinate conversion rule, first, the vector a is converted to a vector a' (=ka) by multiplying the vector a by a coefficient k. Moreover, a vector a' is represented by (dx, dy) in XY Cartesian coordinates and is the added X component (dx, 0) and Y component (0, dy). Here, the starting point and end point of the vector a' are represented by P and P', respectively. Furthermore, the distance from the central point O of a sectoral portion in an ultrasonogram 31 to point P is represented by D. Furthermore, the angle made by the vertical line passing through the central point O and a beam line containing a straight line OP is represented by Θ. The information regarding D and Θ is held as the information regarding the depth and line address with which the line address and depth storage portion 17 is related.

First, the angle β made by the horizontal line passing through point P and a straight line PP' is represented by formula 1.

$$\beta = \tan^{-1}\left(\frac{dy}{dx}\right) \tag{1}$$

Furthermore, the angle α made by a beam line containing a straight line OP and a vector PP' is represented by formula 2.

$$\alpha = 90° - \beta - \Theta \tag{2}$$

Furthermore, the distance l between P and P' is represented by formula 3.

$$l = \sqrt{(dx)^2 + (dy)^2} \tag{3}$$

Furthermore, the angle θ made by the beam line where point P before movement is located or the straight line and a beam line where point P' after movement is to be located is represented by formula 4.

$$\theta = \tan^{-1}\left(\frac{l \cdot \sin\alpha}{D}\right) \tag{4}$$

On the other hand, the amount of change from the depth at point P before movement to the depth at point P' after movement is represented by formula 5.

$$d = l \cdot \cos\alpha \tag{5}$$

Then, the calculation portion 25 determines the line address of a beam line where point P' after movement is located based on the angle θ according to formula 4. For example, in the case of the present embodiment, since each beam line is set so as to be one degree away from neighboring lines, for example, if θ is two degrees, a beam line at a location two beam lines away from the original beam line is set as a beam line after movement and its line address is obtained.

Furthermore, in the calculation portion 25, the amount of change d of the depth of formula 5 is sought and, based on the result, the depth of point P' after movement is sought. That is, a depth obtained by subtraction of d from the depth D at point P before movement is made a depth of point P' after movement.

Moreover, in FIG. 3, in the interests of simplicity, since the vector a' and the angle θ are largely illustrated, the position of point P' is out of the beam line making an angle with the line OP. However, since actual calculation is performed at every small time interval, both vector a' and angle θ are very small and changes where the position of point P' comes off the beam line making the angle θ with the line OP are as small as negligible.

Figure 4:
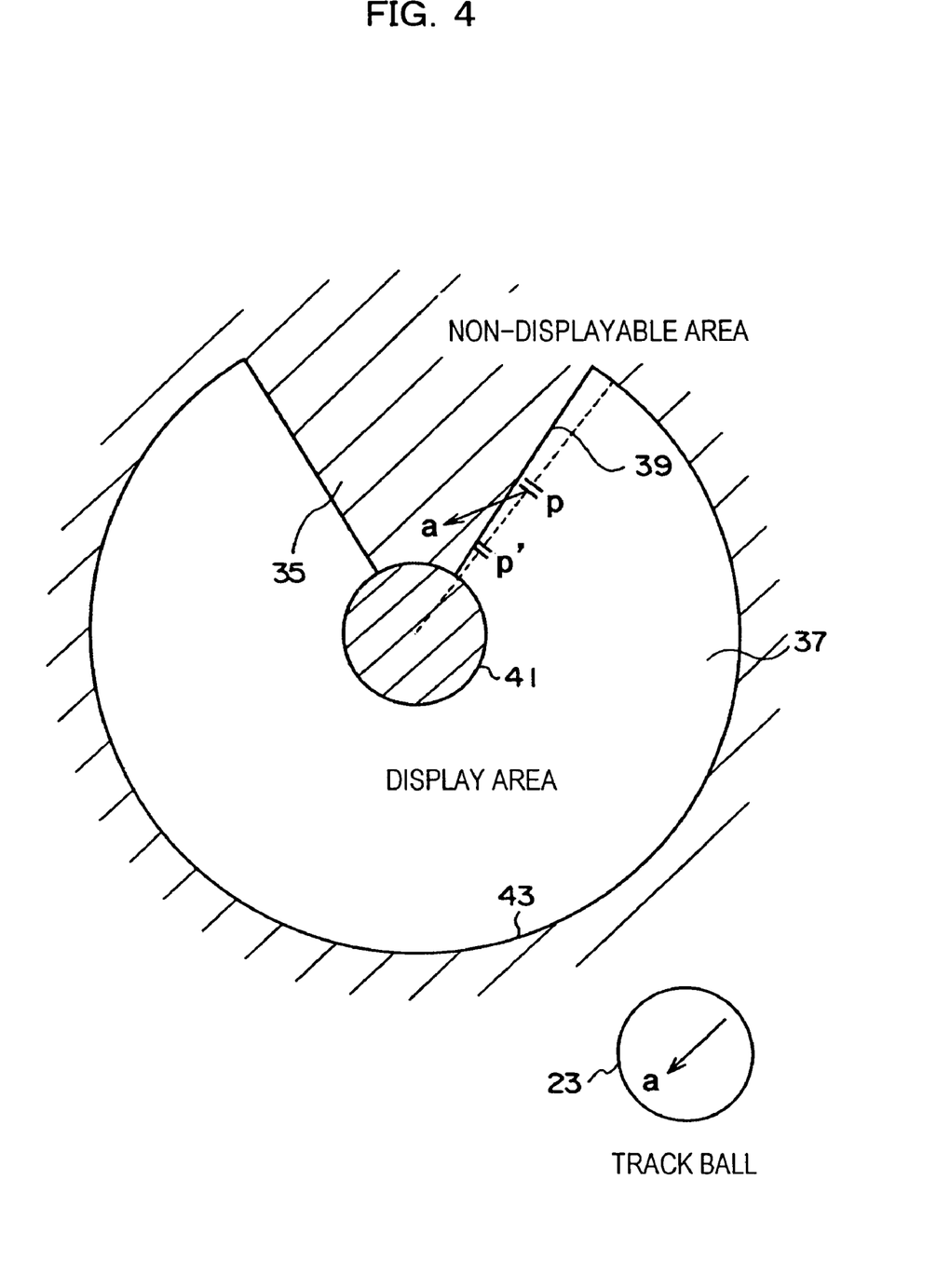
FIG. 4 shows one example of the display screen where a destination of movement is decided when the destination of movement is in a non-displayable area.

Next, in step S03, the calculation portion 25 judges whether or not the beam line according to the line address sought in step S02 can be displayed. For example, as shown in FIG. 4, when an area where the central angle of a sectoral portion is 300° is scanned by an ultrasonic beam, a non-displayable sectoral area 35 of a central angle of 60° exists. In this case, there are cases where a line address at which the point P' after movement sought in step S02 is located is included in the non-displayable area 35. In this case, the process proceeds to step S04 and, except for that, the process proceeds to step S05.

In step S04, out of beam lines contained in the display area 37 shown in FIG. 4, the calculation portion 25 sets the line address of a beam line the closest to the beam line according to the line address sought in step S02 instead of the line address sought in step S02, and the process proceeds to step S07. As a result, point P' after movement moves along the outer edge portion 39 of the display area 37 on the screen.

Figure 5:
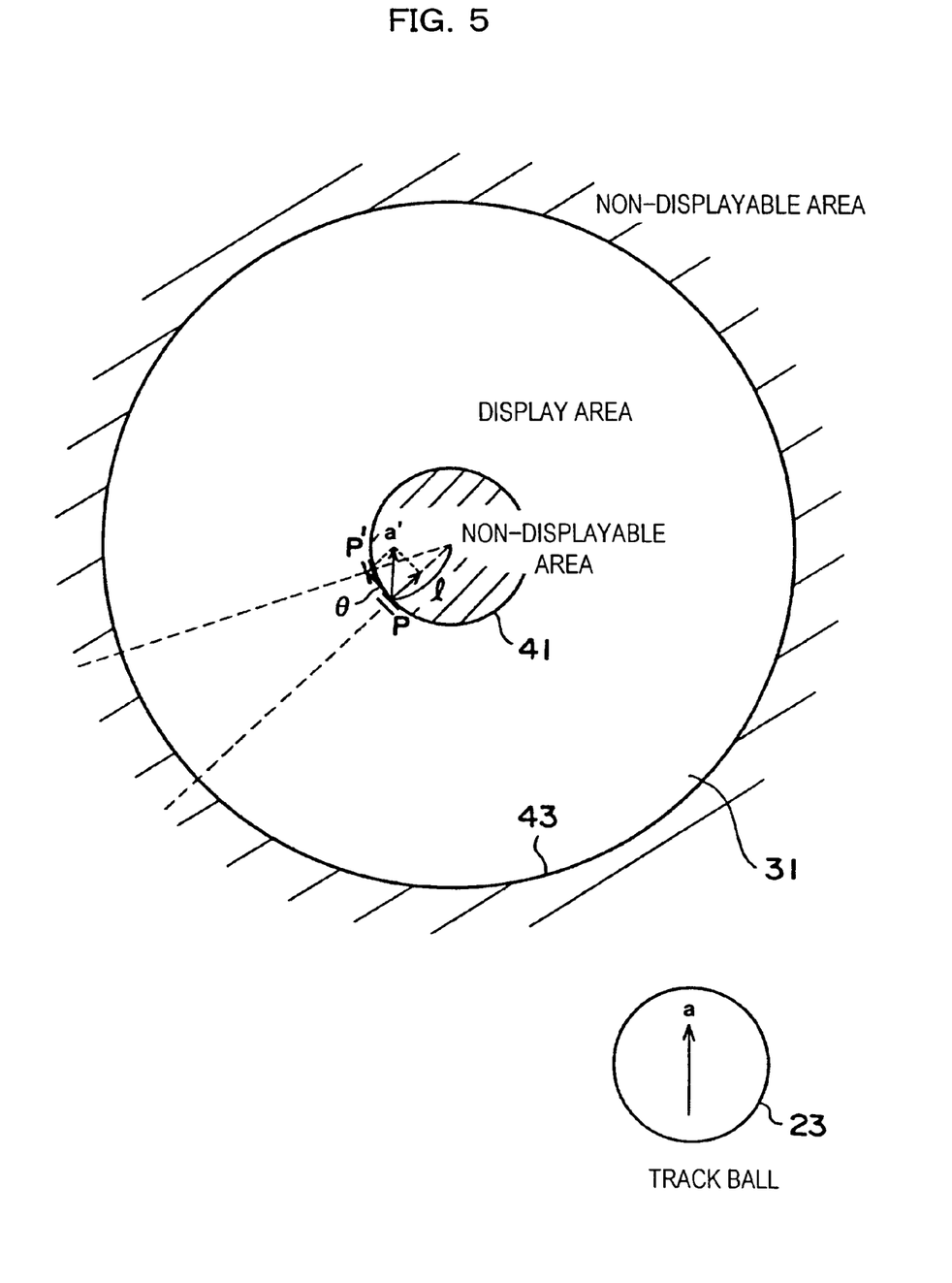
FIG. 5 is to describe the processing of the present invention when the depth of point P' after movement is the minimum depth or less in a non-displayable area.
Figure 6:
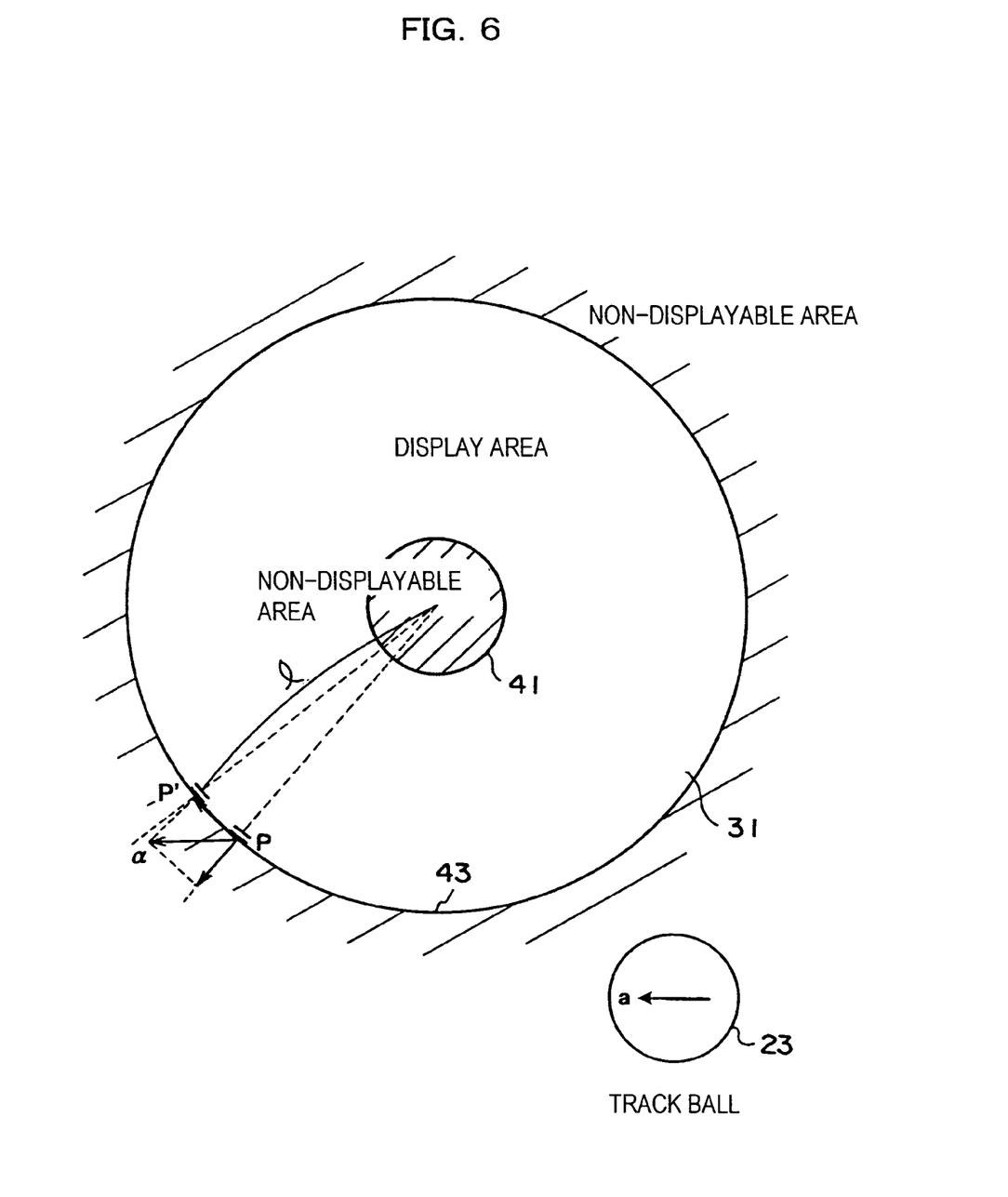
FIG. 6 is to describe the processing of the present invention when the depth of point P' after movement is over the maximum in a non-displayable area.

Furthermore, in step S05, the calculation portion 25 judges whether or not the position of the depth sought in step S02 is contained in the display area. That is, as shown in FIG. 5, it is judged whether or not the position of the depth is in the non-display area more inner than the inside circle 41 in the circular B-mode image corresponding to the outer surface of the probe 1 since the depth is too small, or, as shown in FIG. 6, it is judged whether or not the position of the depth is in the non-display area more outer than the outside circle 43 in the display area in the circular B-mode image as the maximum shooting area determined in accordance with the PRF in advance since the depth is too large, for example. When the depth is in the non-display area, the process proceeds to step S06, and, in other cases, the process proceeds to step S07.

In step S06, as shown in FIG. 5, when the depth is too small, the calculation portion 25 sets the minimum depth which can be displayed instead of the depth sought in step S02, and the process proceeds to step S07. As a result, on the screen, point P' after movement moves along the circle 41 having the minimum depth which can be displayed. On the other hand, as shown in FIG. 6, when the depth is too large, the calculation portion 25 sets the maximum depth which can be displayed instead of the depth sought in step S02, and the process proceeds to step S07. As a result, point P' after movement moves along the circle 43 showing the maximum depth which can be displayed.

Then, in step S07, the calculation portion 25 inputs the line address and depth of point P' after movement sought in step S02, S04, and S06 to the line address processing portion 27 and the depth setting portion 29. Then, these line address and depth are input to the Doppler processing portion 13 and set as the position of the Doppler sample gate after movement. Furthermore, a mark for displaying the Doppler sample gate is generated by the display body output portion 30 and this mark superimposed on the B-mode image is displayed on the display portion 9. Furthermore, these line address and depth are input to the line address and depth storage portion 17 and the line address and depth held up to that time is replaced with the new line address and depth.

As described above, according to the present embodiment, the position of a Doppler sample gate as a display body is stored in connection with the address and depth of a beam line and displayed. Then, the calculation portion 25 resolves the amount of movement input from the track ball 23 with reference to the beam line and depth before movement into a component in the direction of the ultrasonic beam line of the ultrasonogram and a component orthogonal to the direction, an ultrasonic beam line after movement is sought based on the resolved orthogonal components, the position of the depth in the ultrasonic beam line after movement is sought based on the resolved component in the direction of the ultrasonic beam line, and thus, the display position of the Doppler sample gate after movement is changed. As a result, regardless of the position of the Doppler sample gate on the B-mode image, the movement of the Doppler sample gate can be made close to the direction of the movement of the track ball, and the feeling of strangeness of the operator is reduced, and the operability can be improved. Furthermore, since the central position of the Doppler sample gate can be located on an ultrasonic beam line, an appropriate measurement can be performed.

Furthermore, when an input takes place such that the Doppler sample gate enters an non-displayable area, since the Doppler sample gate is made to move along the outer edge portion of a display area, the Doppler sample gate does not disappear from the screen and accordingly, the operator does not lose sight of that and, as a result, the operability is more improved.

Figure 7:
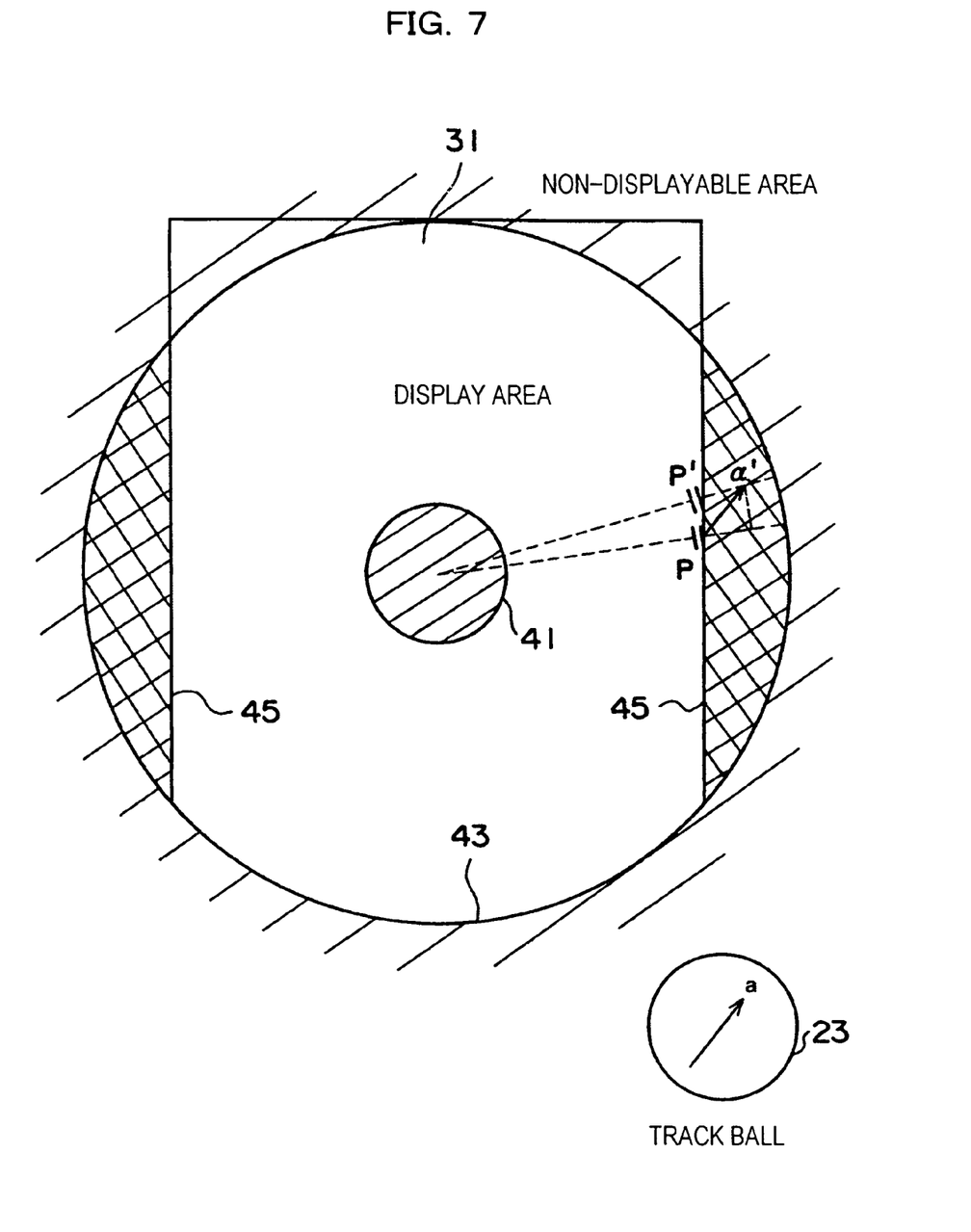
FIG. 7 is to describe the processing of the present invention when there is a non-displayable area because of a screen specification.

Furthermore, in the above-described embodiment, regarding whether or not the line address can be displayed and the depth can be displayed, only restrictions on the transmission and reception of ultrasonic waves were considered, but, except of these, restrictions based on the requirements of the monitor may be considered. FIG. 7 shows one example of screen displays where there are restrictions based on such screen specifications and the operation of a track ball. As shown in FIG. 7, when the display area is limited because of screen size, there are non-display areas, and, in this case, the combination of depths or line addresses related to such area is input to the input amount and output position calculation portion and, when the point P' after movement sought in step S02 is contained in such areas, they may be changed to a line address and depth in the area which is the closest to the input P' after movement and may be displayed. Thus, even if the instruction is wrongly input to move the Doppler sample gate into an non-displayable area, the Doppler sample gate does not disappear from the screen and stops at the outer edge portion of the display area, and accordingly, the operator is prevented from losing sight of the Doppler sample gate and the operability can be more improved.

Figure 8:
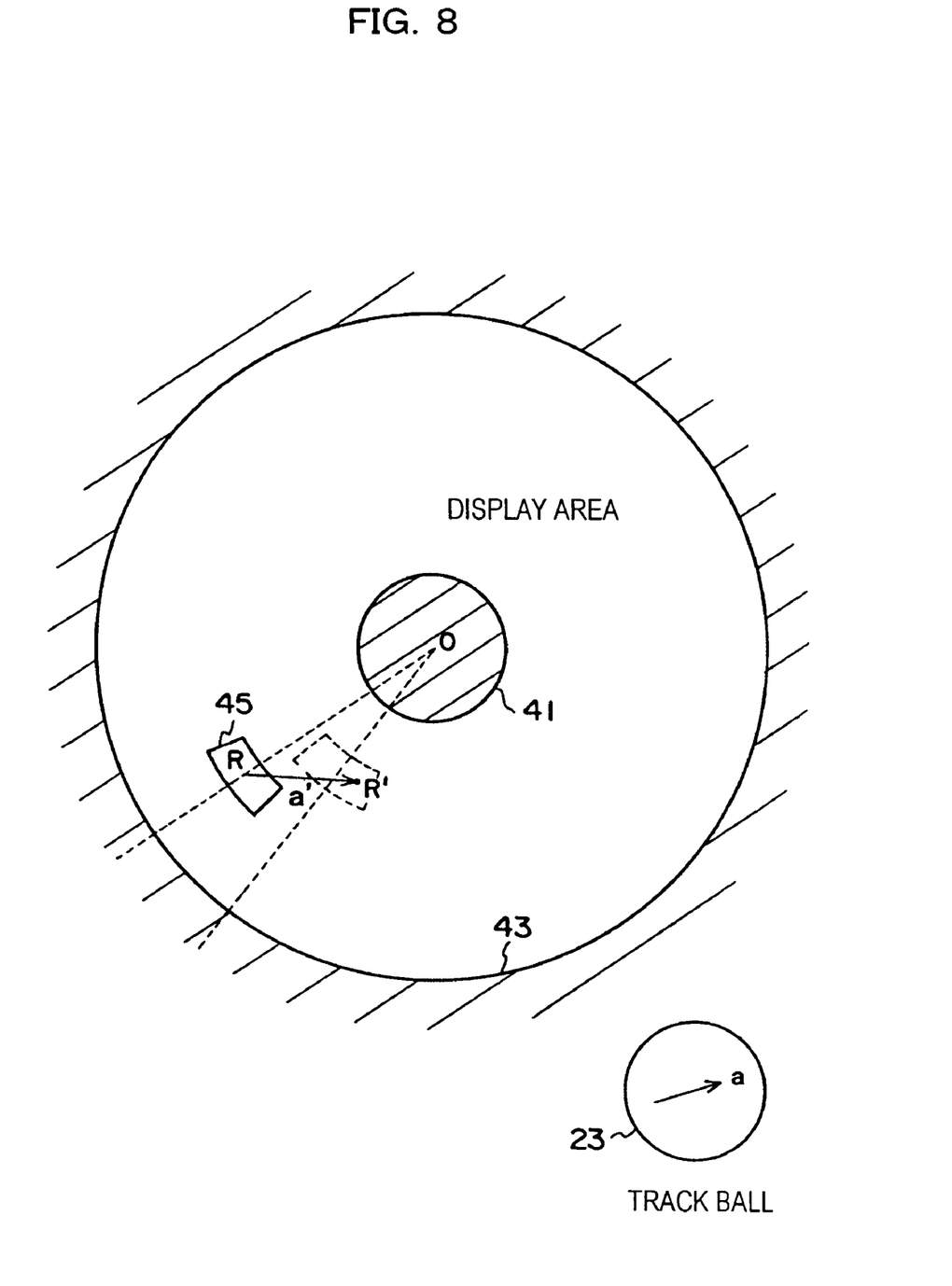
FIG. 8 shows one example of the screen display when the operation of movement of a Doppler color box is performed in an ultrasonograph of the present invention.

Furthermore, the same method as the above-described method for setting the Doppler sample gate may be used for moving a Doppler color box. FIG. 8 shows the operation of a track ball and the screen display when a Doppler color box is moved in an ultrasonograph in which the present invention is applied. The Doppler color box is a specified area where a part of the area of a B-mode image is specified and a color flow mapping image as a color Doppler image, in which blood flow velocities, etc., sought in Doppler mode are classified by color and displayed, superimposed on the B-mode image is displayed. The Doppler color box is generally defined such that the upper and lower limits of depths and the area of line addresses are specified and, as a result, the shape of the Doppler color box is sectoral as shown in FIG. 7. Then, when the beam address and depth related to, for example, the central point R of the Doppler color box are dealt with in the same way as in the setting of the Doppler sample gate described above, the Doppler color box can be moved. Furthermore, the M-node sample gate may be set by the same method.

Furthermore, the present invention can be applied not only to the setting of the position described above, but also to the alteration, expansion, or reduction of the areas such as the Doppler color box, the B-mode shooting area, etc. In this case, the boundary line of the outer edge portion of the Doppler color box and the B-mode shooting area, and Points representing the boundary, for example, points on the boundary line and points at the corners of the area are made display bodies, and, when these are moved by a track ball, etc., in the same way as in the above-described Doppler sample gate, the alteration, expansion, or reduction of the area can be made.

In the above embodiment, a method for controlling movement of a display body was described in accordance with the coordinate conversion rule suited for an ultrasonogram of a wide-angle sectoral portion or a circular portion, for example, but the present invention is not limited to the rule and the rule can be modified as described next. That is, in the case of a conventional ultrasonogram in which the central angle of a sectoral portion is 120° or less, it is considered that a method for controlling movement of the display body in accordance with the conventional coordinate conversion rule is accustomed to use. Then, when the central angle of a sectoral portion in the ultrasonogram is a set value (for example, 120°) or less, the conventional coordinate conversion rule (first coordinate conversion rule) is applied, and when the central angle of a sectoral portion exceeds a set value, the coordinate conversion rule of the present invention (second coordinate conversion rule) can be applied. In this case, the first and second coordinate conversion rules are set in the calculation portion 25 in FIG. 1. The calculation portion 25 compares the central angle of a sectoral portion in an ultrasonogram given by the control portion 19 with a set value, and either of the first and second coordinate conversion rules is applied. Then, the ultrasonograph becomes convenient to use.

The invention claimed is:

1. An ultrasonograph comprising:
an ultrasonogram generating portion for generating an ultrasonogram based on a reflection echo signal obtained by radially scanning a specimen irradiated with an ultrasonic beam and a display area;
a monitor screen for displaying the generated ultrasonogram;
a display-body image generating portion for generating an image of a display body superimposed on the ultrasonogram;
means for storing a first display position of the display body displayed on the monitor screen;
an input portion for inputting the amount of movement of the display body from the first display position to a second display position;
calculation means for determining the second display position of the display body based on the amount of movement input from the input portion and the display area; and
means for moving the display body from the first display position to the second display position determined by the calculation means, wherein
the calculation means decomposes the amount of movement input from the input portion into a component in the direction of an ultrasonic beam line of the ultrasonogram and a component orthogonal to the former component,
the ultrasonic beam line of the second display portion is determined based on the component orthogonal to the former component, and the depth position on the ultrasonic beam line of the second display position is determined based on the component in the direction of the ultrasonic beam line.

2. An ultrasonograph according to claim 1, wherein the calculation means contains a storage portion for storing the first display position of the display body through the position of the ultrasonic beam line and a depth on the ultrasonic beam line.

3. An ultrasonograph according to claim 1, wherein
the amount of movement is input from the input portion in accordance with XY Cartesian coordinates,
the calculation means decomposes the amount of movement in accordance with the XY Cartesian coordinates,
the display body moves from the first display position to the ultrasonic beam line of the second display portion, and
the depth position on the ultrasonic beam line of the second display position is determined based on the component in the direction of the ultrasonic beam line.

4. An ultrasonograph according to claim 1, wherein the display body is a Doppler sample gate made up of a pair of line bodies opposite to each other, and the display-body image generating portion generates an image in which the pair of line bodies are displayed so as to be orthogonal to the ultrasonic beam line.

5. An ultrasonograph according to claim 1, wherein the display body is a Doppler color box marking off the display area of a color flow mapping image, and the ultrasonogram generating portion contains means for generating a color flow mapping image showing the state of a blood flow in the Doppler color box and making the image displayed in the Doppler color box on the monitor screen.

6. An ultrasonograph according to claim 1, wherein the display body is a frame body for marking off an interest area.

7. An ultrasonograph according to claim 1, wherein the calculation means determines a second display position of the display body based on a coordinate transformation rule set in advance, and the coordinate transformation rule is separately set for a case where the central angle of a sectoral or circular portion of the ultrasonogram is a set value or less and for a case where the central angle of the sectoral or circular portion of the ultrasonogram is above the set value.

8. An ultrasonograph according to claim 7, wherein the set value of the central angle is 120°.

9. An ultrasonograph according to claim 7, wherein the coordinate transformation rule contains a first coordinate transformation rule to be applied to a case where the central angle of a sectoral portion of the ultrasonogram is a set value or less and a second coordinate transformation rule to be applied to a case where the central angle of the sectoral or circular portion of the ultrasonogram is above the set value, wherein, in the first coordinate transformation rule, the direction of one axis of the amount of movement input from the input portion corresponds to a depth in the direction of an ultrasonic beam line and the direction of the other axis corresponds to the direction orthogonal to the direction of the ultrasonic beam line, and wherein, in the second coordinate transformation rule, the amount of movement input from the input portion is decomposed into a component in the direction of an ultrasonic beam line and a component orthogonal to the ultrasonic beam line, an ultrasonic beam line at a second display position of the display body is determined based on the component orthogonal to the ultrasonic beam line, and a depth position on the ultrasonic beam line at the second display portion is determined based on the component in the direction of the ultrasonic beam line.

10. An ultrasonograph according to claim 1, wherein the calculation means contains a first conversion means which determines a second display position of the display body in accordance with a coordinate transformation rule where the direction of one axis of the amount of movement input from the input portion corresponds to a depth in the direction of an ultrasonic beam line and the direction of the other axis corresponds to the direction orthogonal to the direction of the ultrasonic beam line and a second conversion means in which the amount of movement input from the input portion is decomposed into a component in the direction of an ultrasonic beam line and a component orthogonal to the ultrasonic beam line, an ultrasonic beam line at a second display position of the display body based on the component orthogonal to the ultrasonic beam line is determined, and a depth position in the ultrasonic beam line at a second display position is determined based on the component in the direction of the ultrasonic beam line, and the display position after movement of the display body is determined by the first conversion means when the central angle of a sectoral portion of the ultrasonogram displayed on the monitor screen is 120° or less and by the second conversion means when the central angle of the sectoral or circular portion of the ultrasonogram is above 120°.

11. An ultrasonograph according to claim 1, wherein the sectoral or circular portion of the ultrasonogram contains non-displayable areas in the central portion and the outer portion, and wherein, when the display position of the display body after movement reaches the non-displayable areas, the display body is displayed on the ultrasonogram close to the display position of the display body after movement.

12. An ultrasonograph according to claim 1, wherein the sectoral portion of the ultrasonogram contains a non-displayable area beyond the central angle of the sectoral portion, and wherein, when the display position of the display body after movement reaches the non-displayable area, the calculation means displays the display body in the side portion of a sectoral portion of the ultrasonogram close to the display position of the display body after movement.

13. A method for controlling movement of a display body of an ultrasonograph, comprising the steps of:
generating an ultrasonogram based on a reflection echo signal obtained by radially scanning a specimen irradiated with an ultrasonic beam and a display area;
displaying the generated ultrasonogram on a monitor screen;
generating an image of a display body superimposed on the ultrasonogram;
storing a first display position of the display body displayed on the monitor screen;
inputting an amount of movement to a second display position from the first display position of the display body;
calculating the second display position of the display body based on the input amount of movement and a display area; and
moving the display body from the first display position to the second display position, wherein
in the step of calculating, the amount of movement input from the input portion is decomposed into a component in the direction of an ultrasonic beam line of the ultrasonogram and a component orthogonal to the ultrasonic beam line, an ultrasonic beam line of a second display position is determined based on the component orthogonal to the ultrasonic beam line, and a depth position of the second display position on the ultrasonic beam line is determined based on the component in the direction of the ultrasonic beam line.

14. A method for controlling movement of a display body of an ultrasonograph as claimed in claim 13, wherein, in the step of calculating, the first display position of the display body is stored through the position of the ultrasonic beam line and a depth on the ultrasonic beam line.

15. A method for controlling movement of a display body of an ultrasonograph as claimed in claim 13, wherein
the amount of movement is input from the input portion in accordance with XY Cartesian coordinates,
in the step of calculating, the amount of movement is decomposed in accordance with the XY Cartesian coordinates,
the display body moves from the first display position to an ultrasonic beam line of a second display position, and
a depth position of the second display position on the ultrasonic beam line is determined based on the component in the direction of the ultrasonic beam line.

16. A method for controlling movement of a display body of an ultrasonograph as claimed in claim 13, wherein the display body is a Doppler sample gate made up of a pair of line bodies opposite to each other, and the display-body image generating portion generates an image in which the pair of line bodies are displayed so as to be orthogonal to the ultrasonic beam line.

17. A method for controlling movement of a display body of an ultrasonograph as claimed in claim 13, wherein the display body is a Doppler color box marking off the display area of a color flow mapping image, and the ultrasonogram generating portion contains means for generating a color flow mapping image showing the state of a blood flow inside the Doppler color box and making the image displayed in the Doppler color box on the monitor screen.

18. A method for controlling movement of a display body of an ultrasonograph as claimed in claim 13, wherein the display body is a frame marking off an interest area.

19. A method for controlling movement of a display body of an ultrasonograph as claimed in claim 13, wherein, in the step of calculating, the second display position of the display body is determined based on a coordinate transformation rule determined in advance, and the coordinate transformation rule is separately determined in a case where the central angle of the sectoral or circular portion of the ultrasonogram is a set value or less, and a case where the central angle is above the set value.

20. A method for controlling movement of a display body of an ultrasonograph as claimed in claim 13, wherein the set value of the central angle is 120°.

* * * * *